United States Patent [19]

Cahiez et al.

[11] Patent Number: 4,983,774
[45] Date of Patent: Jan. 8, 1991

[54] PREPARATION OF KETONES BY THE ACYLATION OF ORGANO-MANGANOUS COMPOUNDS

[75] Inventors: Gérard Cahiez, Paris; Blandine Laboue, Paris Cedex; Pierre Tozzolino, Morlaas, all of France

[73] Assignee: Societe Nationale Elf Aquitaine, France

[21] Appl. No.: 285,713

[22] Filed: Dec. 16, 1988

[51] Int. Cl.$^5$ .............................................. C07C 45/45
[52] U.S. Cl. .................................... 568/319; 568/323; 568/354; 568/355; 568/364; 568/397; 568/407
[58] Field of Search ............... 568/397, 407, 319, 323, 568/354, 364, 355

[56] References Cited

U.S. PATENT DOCUMENTS

| | | | |
|---|---|---|---|
| 4,298,542 | 11/1981 | Yoshida | 568/318 |
| 4,827,044 | 5/1989 | Tozzolino et al. | 568/319 |

FOREIGN PATENT DOCUMENTS 59-199650  11/1984  Japan .................................. 568/407

OTHER PUBLICATIONS

Friour et al, Tetrahedron, vol. 40, pp. 683–693 (1984).
Friour et al, Chem. Abstr., vol. 103, #22150w (1985).
Friour et al, Chem. Abstr., vol. 100, #138,559d (1984).

*Primary Examiner*—James H. Reamer
*Attorney, Agent, or Firm*—Ostrolenk, Faber, Gerb & Soffen

[57] ABSTRACT

The preparation of ketones by reacting an acylating agent with an organo-manganous compound is catalyzed by a copper compound.

16 Claims, No Drawings

PREPARATION OF KETONES BY THE ACYLATION OF ORGANO-MANGANOUS COMPOUNDS

The invention relates to an improvement in the known process which consists of producing a ketone by the action of an acylation agent in an organic solvent on an organo-manganous compound, in particular on a mixed organo-manganous compound.

This known process provided an important advance in the technique concerned and allows the preparation of a large number of very diverse ketones, which can carry various functional groups or others. The use of mixed organo-manganous compounds has rendered possible operation under milder conditions, which are more practical industrially than those of the prior art. Useful information on this subject is found in an article by G Cahiez "Les Organo-manganeux: utilisations en synthèse organique", in "L'Actualité Chimique" of September 1984. A table of 24 types of ketones is given there, amongst others, which show the diversity of the products which it is possible to obtain by the process in question, in good yields.

It is known in particular that iodised organo-manganous compounds are easily acylated by an acid chloride in ether. This reaction allows the preparation with good yields of numerous ketones. However, the preparation of complex ketones starting from an iodised organo-manganous compound having a tertiary or secondary alkyl group requires particular precautions because of the instability of these compounds; large excesses of the organo-manganous compound, complexing of the organo-manganous compound with tetrahydrofuran, reduction of the temperature to −40° C. Despite all these precautions, the corresponding complex ketones are obtained with relatively middling yields. Moreover, irrespective of the results obtained, economic considerations in general preclude the use of iodised organo-manganous compounds on the industrial scale.

It is also known that most chlorinated organo-manganous compounds (particularly those which do not have a secondary or tertiary alkyl group) are acylated by symmetrical anhydrides in tetrahydrofuran with suitable yields, though somewhat lower than those which are obtained with iodised organo-manganous compounds in ether. However, the use of a symmetrical anhydride has the disadvantage of utilising only one of the acyl residues employed.

In general, the use of other acylating agents, such as mixed anhydrides and acid chlorides, has long posed problems ("Activite des organo-manganeux", TETRAHEDRON, vol. 40, No 4 page 683 to 693, 1984). In effect, during the reaction of a mixed anhydride with a chlorinated organo-manganous compound in tetrahydrofuran, it is found that a major part of the ester forms alongside the ketone. As regards acid chlorides, after certain problems caused by opening of the tetrahydrofuran ring in the presence of manganese salts, the operative precautions have allowed their use in a large number of cases; however, the preparation of certain ketones has proved to be impossible under these conditions in acceptable yields. In particular, the reaction of an acid chloride in tetrahydrofuran with organo-manganous compounds RMnCl, in which R is a methyl group, secondary or tertiary alkyl or aryl leads to mediocre or virtually zero yields.

The improvement provided by the present invention allows these disadvantages to be remedied with good yields of the ketone, whatever the acylation agent utilised and the structure of the organo-manganous compound.

The process according to the invention, which consists in producing a ketone by the action of an acylation agent on an organo-manganous compound in an organic solvent according to the reaction:

$$RMnX + R'COZ \xrightarrow{\text{organic solvent}} R-CO-R' + MnXZ, \quad (1)$$

is characterised in that a monovalent or divalent copper compound is introduced into the medium. It is preferable to effect this introduction at the beginning of the reaction.

Among copper compounds utilisable according to the invention, it is of interest to employ those which are the most easily accessible in practice, particularly the chlorides, bromides, acetates, propionates, stearates or other aliphatic acid salts.

While the proportion of the cuprous or cupric catalysts can vary widely, it is in general from 1 to 10 atoms of copper per 100 moles of organo-manganous compound and preferably 2 to 6 atoms.

The beneficial effects of the addition of a cuprous or cupric catalyst are given with numerous organo-manganous compounds and with various acylation agents, if the acylation is effected at temperatures between −50° C. and the ambient, with the addition of the catalyst as indicated above.

The acylating agents R'COZ according to the invention are those which may be acid halides R'COX (X=halogen), anhydrides (R'CO)$_2$O, R'COOCOR'', R'COOCOOR'', R' and R'' being the same or different and can be very varied organic groups, particularly aliphatic, aryl, cycloaliphatic etc., which can carry functional groups. The improvements provided by the invention are particularly clear in the case of acid chlorides and mixed anhydrides.

The organo-manganous compounds RMnX according to the invention can be mixed organo-manganous compounds, X being a halogen, R an organic group, particularly aliphatic, aryl or cycloaliphatic which can if required carry functional groups. The improvements provided are particularly clear in the case where X is Cl and where R is a methyl, secondary or tertiary alkyl or aryl group. While the improvement according to the invention applies particularly well to the preparation of ketones starting from mixed organo-manganous compounds, it can be employed in the case of other organo-manganous compounds, such as for example R$_2$Mn, R$_3$MnLi, R$_4$MnLi$_2$, R$_3$MnMgX, R$_4$Mn(MgX)$_2$.

According to a variant of the invention, the organo-manganous compound is produced as a reaction intermediate by the acylation in a suitable solvent of an organo-metallic compound RMX, M being a metal of one of the Groups I-III and VI-VII of the Periodic Classification of the Elements and X being a halogen or a second group R, by a compound R'COZ, in the presence of a manganese salt and a copper salt in catalytic quantities. Preferably, the organo-metallic compound is an organo-magnesium compound and the manganese salt is solubilised by the addition of an alkaline salt of a quaternary ammonium salt, which gives a complex of the type MnX$_2$.nM'Y, where X is an anion, preferably a halogen, M' is an alkaline metal cation or a quaternary ammonium group, Y is an anion of the same type as X, but not necessarily identical, and n is usually from 1 to 4. In THF, when the organo-magnesium compound is RMgCl and the Mn salt is complexed by LiCl, for example in the form $MnCl_2.2LiCl$, an organo-manganous compound of the type $R_4Mn(MgCl)_2$ is produced as a reaction intermediate. This variant gives very good results, when R'COZ is an acid halide or a mixed halide, and the presence of the Cu salt allows the yields of ketones produced by acylation to improve, particularly in the case of complex ketones.

As regards the other parameters of the process, they are the same as in the prior art. Thus, as regards the solvent, this is preferably constituted by an ether, in particular a cyclic ether such as tetrahydrofuran. Mixtures of ethers can be used with other solvents, for example ethyl acetate, ethyl carbonate, acetonitrile or aliphatic or aromatic hydrocarbons, for example benzene, toluene, hexane, cyclohexane etc. The concentrations of the compounds reacting in the solvent can vary, but it is useful to operate with solutions and/or suspensions containing 0.1 to 2 mole of each of these compounds per litre of solvent or preferably 0.3 to 0.7 mole/litre.

The examples given below show gains in yield obtained in different cases of use of the process according to the invention. They have been carried out under the following conditions, where the organo-manganous compound is RMnCl.

To a suspension of 52 mmoles of RMnCl in 100 ml of THF, 2.5 mmoles of CuCl is added and then 50 mmoles of an acid chloride R'COCl, with agitation in the absence of air. This operation takes place between 10° C. and −50° C. The reaction medium is then allowed to warm up to the ambient temperature and is agitated for 2 hours. After this time, the medium is cooled to −10° C. and 60 ml of an aqueous 1N HCl solution is added, to eliminate the Mn salts. The aqueous phase is decanted and the organic materials Y contained in it are extracted twice with 50 ml of ether. The combined organic phases are then washed with 50 ml of an aqueous saturated solution of $NaHCO_3$. After drying over $MgSO_4$ and evaporation of the solvents under vacuum, the ketone formed is separated by distillation.

When the acid chloride is replaced by a mixed anhydride, the mode of operation is the same.

EXAMPLES 1 TO 8

In this series of tests, octanoic acid chloride $C_7H_{15}$-COCl is reacted with various mixed organo-maganous chlorides RMnCl in THF, the temperature at the time of mixing being indicated in the Table below. In each case using the mode of operation described above, a test is carried out without a catalyst and with 5 atoms of $Cu^+$, in the form of CuCl, per 100 moles of acid chloride utilised. The Table gives as results the yields in the ketone R-CO-$C_7H_{15}$ obtained in each case by the reaction:

TABLE I $RMnCl + C_7H_{15}COCl \longrightarrow RCOC_7H_{15} + MnCl_2$

| Ex. | R | Temperature | CuCl | Yield % |
|---|---|---|---|---|
| 1 | $(CH_3)_2CH-$ | −50° C. | — | 69 |
| 2 | " | " | present | 93 |
| 3 | $(CH_3)_3C-$ | " | — | 0 |
| 4 | " | " | present | 92 |
| 5 | $C_6H_5-$ | −20° C. | — | 55 |
| 6 | " | " | present | 63 |
| 7 | $CH_3$ | " | — | 40 |
| 8 | " | " | present | 91 |

A considerable improvement in the yield is confirmed in the preparations carried out in the presence of CuCl. It is surprising in the case of the tert.butyl (examples 3 and 4), the steric hindrance effect is not observed in the presence of a $Cu^{30}$ catalyst.

EXAMPLES 9 AND 10

Analogous preparations to those of the foregoing examples are effected with a less reactive acid chloride, that of benzoic acid, $C_6H_5$-COCl, which is mixed in THF at 0° C. with tert.butyl manganese chloride, the yield of tBuCOPh is practically nil; with 5 moles CuCl per 100 moles of $C_6H_5COCl$, it rises to 77%, a most remarkable effect.

EXAMPLE 11

Comparative test for Examples 1 and 2.

Up to the present, by the known technique, the best results for the preparation of isopropyl heptyl ketone were obtained by the action of 1 mole of octanoic acid chloride $C_7H_{15}COCl$ on 1.5 mole of isopropyl manganese iodide $(CH_3)_2CH-Mn-I$ complexed in 5 equivalents of THF, the mixture being formed between −30° and −40° C. A yield of 71% is obtained in contrast to the 69% of Example 1, obtained with 1 mole of $(CH_3)_2CH-Mn-Cl$. The 93% attained in Example 2 due to the catalyst CuCl is of considerable interest not only through the increase in the yield by 22%, but also because of the use of organo-manganous chloride which is less expensive and more stable than the corresponding iodide.

EXAMPLES 12 TO 16

In this series of tests, different mixed anhydrides R'-COO-COOC$_2$H$_5$ are reacted with various organo-manganous compounds RMnCl in THF, the temperature at the moment of mixing ranging between −10° C. and 20° C., in the presence of 3% molar (with respect to the anhydride) of CuCl. Table II gives as results the yields obtained in the ketone R-CO-R'.

TABLE II

| Ex | R | R' | Yield % |
|---|---|---|---|
| 12 | Butyl | Heptyl | 81 |
| 13 | Butyl | $(CH_3)_2-C=CH$ | 76 |
| 14 | Butyl | Phenyl | 60 |
| 15 | t-Butyl | Heptyl | 76 |
| 16 | Phenyl | Heptyl | 78 |

EXAMPLE 17

Under conditions similar to those of Example 12, in the absence of CuCl, $C_7H_{15}$-COO-COO$C_2H_5$ is reacted with $C_4H_9MnCl$; the yield in ketone is of the order of 30%. Also, the reaction is slightly reproducible. It has been shown that the addition of CuCl to Example 12 allows a notable improvement in the yield.

The examples given below show the gains in yield obtained in the case where the organo-manganous compound is produced as a reaction intermediate by acylation of an organo-magnesium compound by a compound R'COCl, in the presence of a manganese salt and a copper salt in catalytic quantities. They have been carried out under the following conditions.

3 mmoles of anhydrous $MnCl_2$ and 6 mmoles of anhydrous LiCl are added to 50 ml of THF at ambient temperature. The mixture is then agitated to give complete dissolution of the salts and there is then added as required 3 mmoles of CuCl (according to the Examples) and finally 100 mmoles of R'COCl. Then 100 mmoles of RMgX is added with the aid of a pump. The temperature of the reaction medium is maintained between 0° C. and 10° C. The duration of this addition is 30 minutes. After the latter, the agitation is maintained for 15 to 30 minutes at ambient temperature, and then the reaction medium is hydrolysed with a dilute HCl solution. The product is then isolated according to standard techniques.

EXAMPLES 18 TO 21

In this series of tests, R'COCl is reacted according to the mode of operation described above with RMgCl in the presence of $MnCl_4Li_2$. In each case, a test has been effected without CuCl and with CuCl. Table III gives the yields of the ketone

obtained.

TABLE III

| Ex | R | R' | CuCl | Yield % |
|---|---|---|---|---|
| 18 | t-Butyl | Heptyl | — | 27 |
| 19 | t-Butyl | Heptyl | present | 80 |
| 20 | Heptyl | t-Butyl | — | 52 |
| 21 | Heptyl | t-Butyl | present | 98 |

This shows, as in the case of acylation of mixed organo-manganous compounds RMnCl by an acid chloride, that the preparation of complex ketones can be effected with even better yields by utilising a catalytic quantity of copper salts.

We claim:

1. A method of producing a ketone comprising reacting an acylation agent selected from the group consisting of acid halides of formula R'COX and mixed acid anhydrides of the formulas $(R'CO)_2O$, R'COOCOR'- and R'COOCOOR" with an organo manganous compound selected from the group consisting of compounds of the formulas, RMnCl, $R_3MnMgCl$, $R_4Mn(MgCl)_2$, where R, R' and R" are organic groups, in an organic solvent, the reaction medium being kept at a temperature of from $-55°$ C. to ambient temperature until a substantial amount of ketone is formed, 1 to 10 moles of a cuprous compound selected from the group consisted of cuprous chloride, bromide, acetate, propionate and stearate per 100 moles of said organo maganous compound being added, while mixing said organo maganous compound with said organic mono-acid chloride or said mixed anhydride, and separating the ketone produced from the reaction mixture.

2. A method according to claim 1, wherein R is an alkyl or an aryl.

3. A method according to claim 2, wherein said acylation agent chloride is R'COCl where R' is a $C_1$ to $C_7$ alkyl or alkenyl, or a phenyl.

4. A method according to claim 3, wherein a mixture of (a) RMnCl or $R_4Mn(MgCl_2)$, and (b) R"COCl in tetrahydrofurane, with a catalytic amount of $Cu_2Cl_2$, is agitated in the absence of air, at a temperature of $-50°$ C. to 0° C., until reaction no longer occurs and the mixture is then allowed to warm up to ambient temperature, agitated for about 2 hours, and again cooled to about $-10°$ C.; an amount of aqueous HCl sufficient to eliminate the $MnCl_2$ present in the mixture is added; the aqueous phase thus formed is separated, the remaining organic phase is washed and dried, and the ketone produced is separated therefrom.

5. A method according to claim 4, wherein the mixture contains 0.1 to 2 moles RMnCl and 0.1 to 2 moles R'COCl per liter of solvent.

6. A method according to claim 2, wherein R is a $C_1$ to $C_7$ alkyl or a phenyl.

7. A method according to claim 6, in which said organo maganous compound is $R_4Mn(MgCl)_2$.

8. A method according to claim 2, wherein said acylation agent is R'COO-COOR" where R' is $C_1$ to $C_7$ alkyl or alkenyl, or a phenyl, and R" is a lower alkyl.

9. A method according to claim 8, wherein a mixture of (a) RMnCl or MgCl and $MnCl_4Li_2$ used jointly, and (b) R'COO-COOR" in tetrahydrofurane, with a catalytic amount of $Cu_2Cl_2$, is agitated in the absence of air, at a temperature of $-10°$ C. to $+20°$ C., until reaction no longer occurs, and then cooled to about $-10°$ C., an amount of aqueous HCl sufficient to eliminate the $MnCl_2$ present in the mixture is added; the aqueous phase thus formed is separated, the remaining organic phase is washed and dried, and the ketone produce is separated therefrom.

10. A method according to claim 9, wherein the mixture contains 0.1 to 2 moles RMnCl and 0.1 to 2 moles R'COO-COOR"per liter of solvent.

11. A method according to claim 2, wherein said organic solvent is selected from the group consisting of tetrahydrofurane, tetrahydrofurane mixed with ethyl acetate, ethyl carbonate, acetonitrile, benzene, toluene, hexane and cyclohexane.

12. A method according to claim 1 wherein said organic solvent is tetrahydrofuran.

13. A method according to claim 12, wherein said organo manganous compound is $R_4Mn(MgCl)_2$ and said $R_4Mn(MgCl)_2$ is formed by the reaction RMgCl and $MnCl_2.2LiCl$.

14. A method according to claim 1 wherein R, R' and R" are optionally substituted aliphatic, aryl or cycloaliphatic groups.

15. A method according to claim 4 wherein said organo maganous compound is $R_4Mn(MgCl)_2$ and said $R_4Mn(MgCl)_2$ is formed by the reaction of RMgCl and $MnCl_2 \cdot 2LiCl$.

16. A method according to claim 9, wherein said organo maganous compound is $R_4Mn(MgCl)_2$ is formed by the reaction of RMgCl and $MnCl_2 \cdot 2LiCl$.

* * * * *